United States Patent [19]
Stein

[11] Patent Number: 5,814,093
[45] Date of Patent: *Sep. 29, 1998

[54] ASSEMBLY FOR FUNCTIONAL ELECTRICAL STIMULATION DURING MOVEMENT

[75] Inventor: Richard B. Stein, Edmonton, Canada

[73] Assignee: Neuromotion Inc., Edmonton, Canada

[*] Notice: The term of this patent shall not extend beyond the expiration date of Pat. No. 5,643,332.

[21] Appl. No.: 718,165

[22] Filed: Sep. 19, 1996

Related U.S. Application Data

[63] Continuation-in-part of Ser. No. 530,603, Sep. 20, 1995.

[51] Int. Cl.$^6$ ........................................................ A61N 1/18
[52] U.S. Cl. .................................................................. 607/49
[58] Field of Search .............................. 607/48, 49, 149, 607/115; 128/649, 782

[56] References Cited

U.S. PATENT DOCUMENTS

| | | |
|---|---|---|
| 3,083,712 | 4/1963 | Keegan, Jr. . |
| 4,381,012 | 4/1983 | Russek ..................................... 607/149 |
| 4,432,368 | 2/1984 | Russek . |
| 4,796,631 | 1/1989 | Grigoryev . |
| 5,487,759 | 1/1996 | Bastyr et al. ............................ 607/149 |

OTHER PUBLICATIONS

W.T. Liberson, M.D., et al., "Functional Electrotherapy: Stimulation . . . ," Read at the 2rd Intl. Cong. of Physical Med., Session on Neuromuscular Diseases, Washington, D.C., Aug. 25, 1960.

A. Kralj et al., "Enhancement of Hemiplegic Patient Rehabilitation . . . ," Prosthetics and Orthotics Intl., vol. 17, pp. 107–114, 1993.

*Primary Examiner*—Scott M. Getzow
*Attorney, Agent, or Firm*—Millen, White, Zelano & Branigan, P.C.

[57] ABSTRACT

The assembly comprises a band, mountable on the leg, carrying all of the components of the assembly to provide a self-contained unit. The components comprise: electrodes for stimulating a leg nerve; a V-shaped plate for conforming with the leg's tibia to reproducibly position the band so that the electrodes are located over the nerve; a tilt sensor for measuring the angular position of the lower leg; a control circuit for processing the sensor signal information and emitting pulses through the electrodes to stimulate the leg in response to phases of body movement; and a battery for supplying power to the tilt sensor, control circuit and stimulator. By comparing the assembly's stimulation states against a known template defining optimal stimulation states, stimulation threshold parameters can be fine tuned without the need for repeated trial and error testing by the user.

7 Claims, 6 Drawing Sheets

ASSEMBLY FOR FUNCTIONAL ELECTRICAL STIMULATION DURING MOVEMENT

CROSS REFERENCE TO RELATED APPLICATION

This application is a continuation-in-part of pending U.S. application Ser. No. 08/530,603, filed Sep. 20, 1995.

FIELD OF THE INVENTION

This invention relates to an electronic stimulator comprising a garment carrying fixed electrodes and means for properly positioning the garment so that the electrodes overlie a nerve to be stimulated. The garment further carries means for monitoring body movement and means for activating the electrodes at appropriate intervals to stimulate the nerve and activate dormant muscles, thereby assisting the body in making a particular movement. For example, the stimulator may be used to assist in overcoming "foot drop" affecting a person who has had a stroke.

BACKGROUND OF THE INVENTION

Functional electrical stimulation (FES) is a method for replacing function, such as walking or grasping, that is partially or completely lost after various lesions to the central nervous system, such as stroke or spinal cord injury.

One of the most common deficits in the lower leg is "foot drop". In this condition, the patient is unable to properly activate the muscles that flex the ankle, to enable the foot to clear the ground during the swing phase of walking. Instead, the foot drops and drags along the ground.

Liberson et al, in a paper entitled "Functional Electrotherapy, Stimulation of the Peroneal Nerve Synchronized with the Swing Phase of the Gait of Hemiplegic Patients" Arch. Phys. Med., 1961, 42, 101–105, first proposed using electrical stimulation to correct foot drop. The authors suggested that the stimulation be controlled by a heel sensor. When the person leaned forward and reduced heel pressure, switch contacts built into the shoe heel would open. Upon opening the switch, current would flow to electrodes positioned over the common peroneal nerve near the knee. The nerve would be stimulated and innervate muscles that flex the ankle. Upon muscle contraction, the foot would flex and clear the ground without dragging during swing. When the heel returned to the ground at the beginning of stance phase, the switch contacts would close and stimulation would be terminated.

A number of variants of the basic system have been tried over the years and some success has been attained. The commonly known prior art electronic stimulators are reviewed in an article by Kralj et al, "Enhancement of Hemiplegic Patient Rehabilitation by Means of Functional Electrical Stimulation"; Prosthet. Orthot. Int., 1993, 17, 107–114.

However, the most common device fitted for people with the condition of foot drop is still an ankle-foot orthosis ("AFO"). An AFO does not involve electrical stimulation. It is a plastic brace that fits around the lower leg and holds the foot fixed, usually at an angle near 90° with respect to the long axis of the leg.

Although AFO's have several disadvantages, the electrical stimulators have not significantly replaced them because the latter have a number of drawbacks. Included among these drawbacks are:

1. that the electrical stimulators comprise a number of pieces, all of which have to be placed and connected together accurately. Carrying this out is a difficult and time-consuming chore for a patient who has likely lost some manual dexterity and who may have suffered some cognitive impairment as a result of stroke or injury. More specifically, these stimulator units typically comprise: (a) a box containing the stimulator, battery and control electronics, which have to be placed on the body or in a pocket; (b) electrodes which have to be placed accurately on the skin; (c) some garment, such as an elastic knee stocking, for supporting the electrodes in place; (d) a foot switch; and (e) wiring connecting the electronics and electrodes;
2. that the lengthy wiring is prone to breakage;
3. that the foot switch may not work reliably on all of several different surfaces such as pavement, carpet, sand, up and down ramps and the like; and
4. that some patients may not land on their heel or put little weight on it, due to spasticity or contractures in the calf muscles. These problems can lead to failure to trigger the stimulation. An alternative is to have a fixed duration of stimulation. This may be appropriate at some speeds of walking or levels of fatigue, but not at others.

With this background in mind, I set out to design an electronic stimulator which is easy to don and doff, which automatically and accurately positions the electrodes, which incorporates sensors that more completely monitor body motion and do not require heel pressure, which uses relatively short connecting wires, and which controls stimulation in response to the stage of body motion.

In developing the invention, I have used a locating means disclosed in U.S. Pat. No. 4,431,368, issued to Russek. This patent teaches a garment carrying a member which closely conforms to the protuberance of the spine. By positioning the member over the spine, electrodes carried by the garment are automatically located accurately over nerves to be stimulated.

SUMMARY OF THE INVENTION

In a first aspect, a stimulator in accordance with a preferred form of the present invention comprises, in combination:

a band of stretchable, breathable fabric having fastening means at its ends for securement of the band around the user's leg in the form of a ring;

anode and cathode electrodes carried by the band in a stationary or fixed condition;

locating means, carried by the band, for cooperating with the bony protuberance of the tibia, to accurately and reproducibly locate the electrodes over the nerve to be stimulated;

tilt sensor means, carried by the band, for measuring the angle of the lower segment of the leg relative to vertical in the sagittal (forward and back) plane and emitting sensor signals indicative thereof;

battery means, carried by the band, for supplying electrical current, as required; and control means, carried by the band and connected with the sensor means, electrodes and battery means, for receiving the sensor signals, processing the sensor signals to establish values indicative of the changing angularity of the limb (that is, position of the lower leg with respect to vertical) and to compare the established values with predetermined adjustable ON and OFF threshold values and initiating and terminating emission of electrical pulses though the electrodes on respectively reaching the ON and OFF threshold values to stimulate the leg muscles in response to phases of body movement.

The band, carrying the components, is compact and thin enough to fit comfortably under pants or other clothing.

The combination of the locating means and fastening means has enabled the assembly to be easily donned with the electrodes correctly located, even when handled by an impaired user. Test trials have shown that the entire assembly can be donned or doffed in less than a minute.

The combination of the tilt sensor with the control means provides a fine degree of continuous leg position monitoring coupled with accurately initiated and terminated stimulation. The result is that stimulation can be closely related to leg position to provide an improved and refined pattern of stimulation, in comparison to prior art FES units. The device provides continuous sensory signals and turns the stimulus on and off regardless of the speed of walking.

Those skilled in the art will realize that certain of the components described can be replaced with equivalents. For example, a resilient C-shaped carrier could replace the band. Another sensor, such as an accelerometer or electric compass, could be substituted for the tilt sensor.

However, the disclosed components are preferred. The elastic band provides good securement and is easily donned and doffed. The tilt sensor provides accurate information even though the user is fat or thin, walks with shoes or in bare feet and walks fast or slow on a variety of surfaces having different inclinations. The tilt sensor further is less sensitive to pathological changes such as contractures or clonus at the ankle, than is the case for a heel switch.

Broadly stated, the invention is a functional electrical stimulator for use on a body limb, comprising: a band, mountable on the limb, for carrying stimulator components; cathode and anode electrodes carried by the band in a fixed condition; means, carried by the band, for reproducibly positioning the band so that the electrodes are located at specified stimulation locations; sensor means, carried by the band in a fixed condition, for measuring the angular position of the limb during movement and emitting sensor signals indicative thereof; control circuit means, carried by the band and connected with the sensor means and electrodes, for receiving the sensor signals, processing the sensor signals to establish values indicative of the changing angularity of the limb and to compare the established values with predetermined adjustable ON and OFF threshold values and initiating and terminating the emissions of pulses through the electrodes when the established values reach the ON and OFF threshold values, to stimulate the limb; and battery means, carried by the band and connected with the sensor means and control circuit means, for supplying electrical power.

In some instances it is preferable to also compare the established values with predetermined adjustable maximum time thresholds and terminate limb stimulation should they be exceeded.

In another aspect of the invention, a patient using the apparatus in combination with a clinician or other means, can generate the data necessary to better define the parameters such as angular ON and OFF threshold values and time thresholds. In a preferred aspect, a hand switch, operated by a clinician, or a limb mounted sensor is used to define the states at which stimulation of the limb is required for proper limb movement. In other words a template is defined for optimal stimulation of the limb. By comparing the limb stimulation states which are actually output by the apparatus and those defined by the template, the parameters used by the apparatus stimulator control circuits can be optimized.

DESCRIPTION OF THE PREFERRED EMBODIMENT

Figure 1:
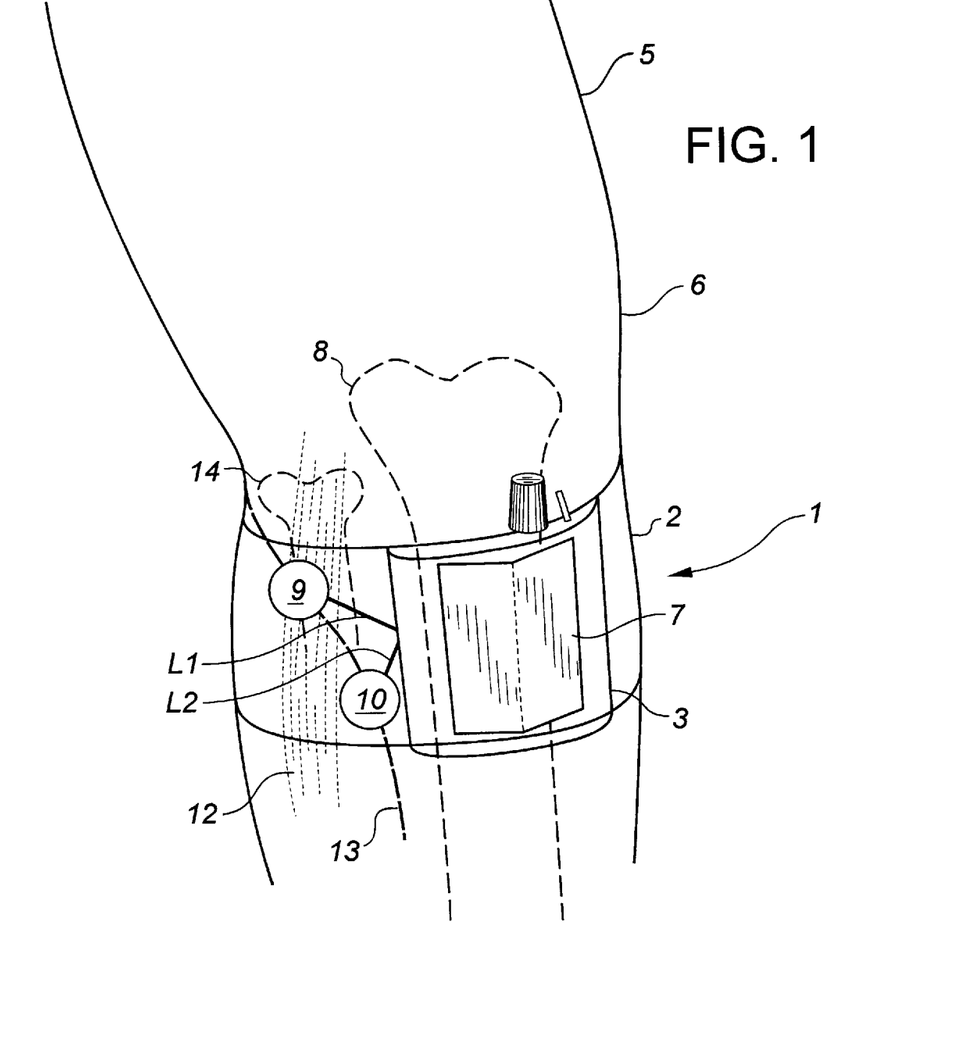
FIG. 1 is a schematic showing the stimulator mounted on a leg with the locations of the tibia and common peroneal nerve shown in dotted lines.
Figure 2:
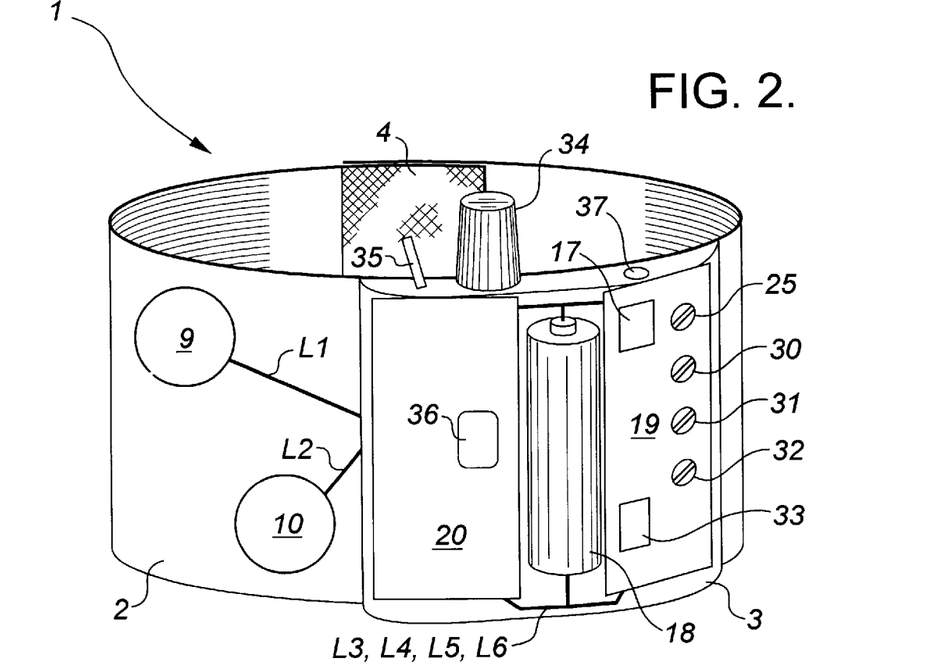
FIG. 2 is a perspective view showing the stimulator with the pouch wall broken away to display the tilt sensor, battery and circuit boards.

Having reference to FIGS. 1 and 2, the stimulator 1, comprises a band 2 made of stretchable, breathable material. One suitable material is perforated neoprene, available from Rubatex Corporation, Bedford, Va. The band 2 forms a pouch 3, for containing stimulator components. Patches 4 of Velcro* fastening material are provided at the band ends to fasten them together, so that the band can form a snug ring around the user's leg 5 below the knee 6.

A V-shaped metal plate 7 is positioned in the pouch 3 and fits snugly therein so as to be fixed along the length of the band. The plate 7 is weakened along its vertical mid-line. It can be readily bent therealong to conform to the anterior position of the tibia 8. The plate may include vertical protrusions which lay parallel to and on opposing sides of the tibia to more positively constrain lateral movement relative to the tibia. Once so bent, the plate 7 can be located reproducibly on the tibia.

Figure 3:
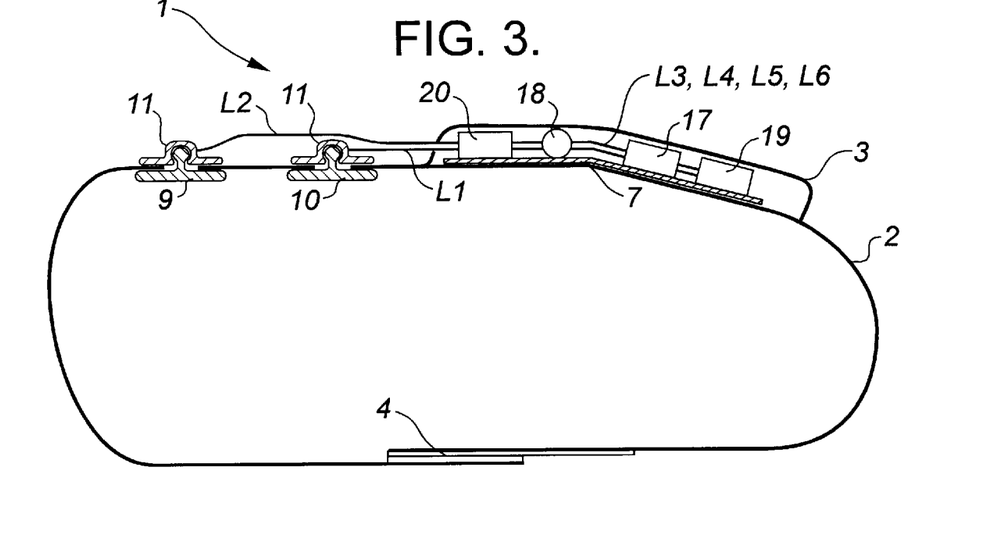
FIG. 3 is a top view of the system, showing connections between the logic circuitry, tilt sensor, battery, stimulator circuits and the electrodes.

Cathode and anode electrodes 9, 10 are attached to the band 2 with conductive snap connectors 11 as shown in FIG. 3.

The optimal placement of the electrodes 9, 10 is determined by a technician or clinician working with the patient. The cathode electrode 9 is usually placed where the common peroneal nerve 13 comes from behind the knee 6 past the head of the fibula 14. Placement of the anode electrode 10 is less critical. It is usually placed further along the course of the nerve 13, where it enters the ankle flexor muscles 12. Once these locations are determined, the band 2 is placed over the electrodes and holes are punched through the fabric with a hole punch. The electrodes contain a male connector that is fitted through the hole and connected with the female connector 11. These female connectors are attached to leads L1, L2.

The electrodes used are of the water-filled cotton type, available from the Josef Stefan Institute, Ljubljana, Slovenia.

In summary then, the band 2 is reproducibly positioned by fitting the plate 7 over the tibia 8, thereby locating the electrodes 9, 10 at the desired positions.

A tilt sensor 17 (otherwise known as an inclinometer) is secured to a printed circuit board containing logic circuit 19 which in turn is attached to the positioning plate 7. Thus, the tilt sensor is fixed with respect to the tibia and the rest of the lower leg. As previously stated, the tilt sensor 17 functions to measure the angle of the lower leg with respect to the vertical in the sagittal plane and emit signals indicative thereof. One suitable sensor for this purpose is available from Midori Inc. Fullerton, Calif., under the designation Model No. UV1.

A 1.5 V AA alkaline or 1.2 V AA NiCd battery 18 for powering the components is attached to the plate 7. The output voltage of the battery 18 is increased to 3 volts by a DC—DC converter 28, for operation of the logic circuit 19. As described below, the battery output voltage is increased through a second converter (not shown) to 5 V and further then to 70 volts by a transformer 29, for operation of the stimulator circuit 20.

The logic circuit 19 and stimulator circuit 20 are mounted to the plate 7 and together comprise control circuit means.

Figure 4:
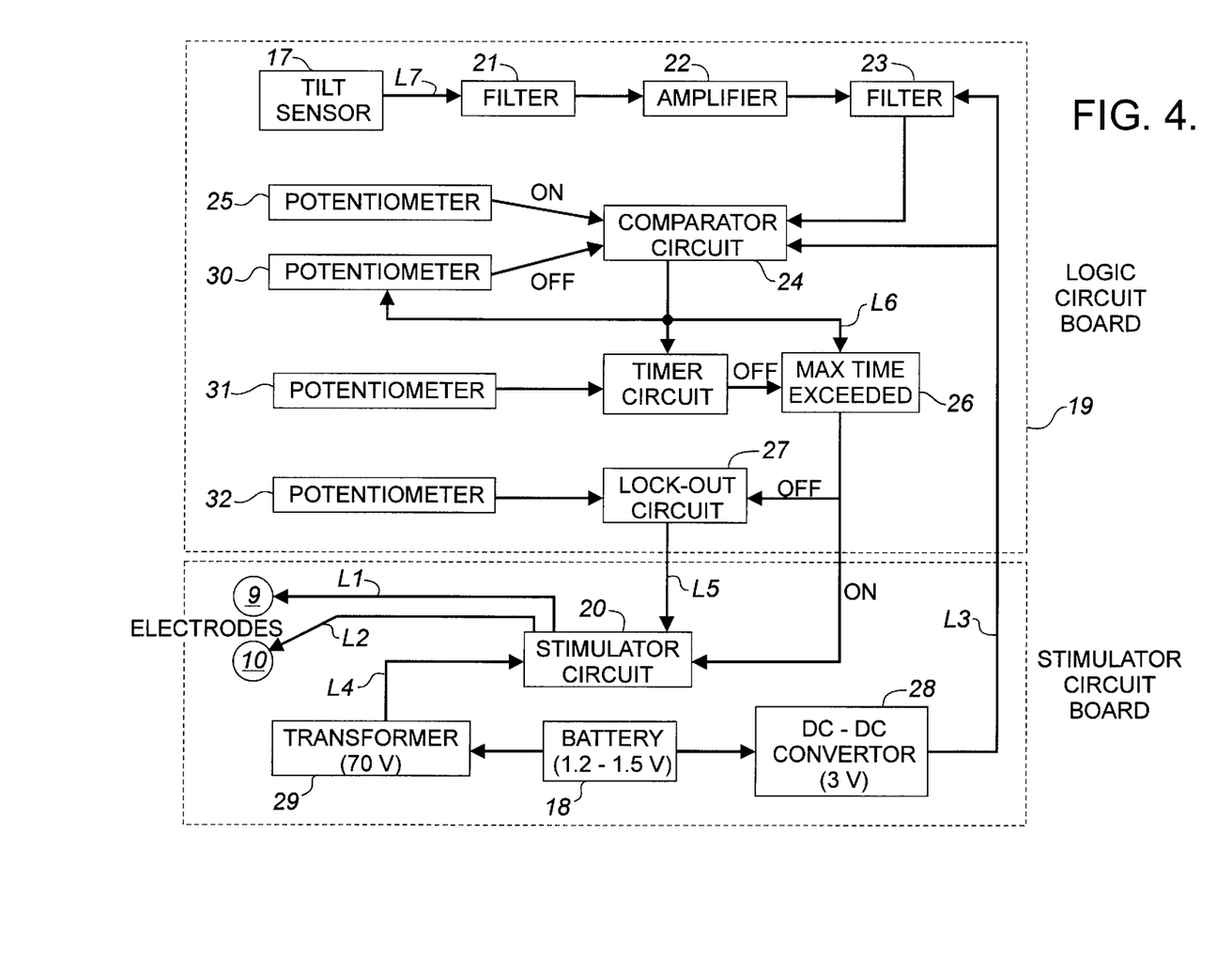
FIG. 4 is a block diagram showing the tilt sensor, logic, power and stimulator circuits and the electrodes.

The logic circuit 19 functions to receive the tilt sensor signals, condition them, compare them to threshold values related to changes in gait and to activate or de-activate the stimulator circuit 20 in response thereto.

As shown in FIGS. 3 and 4, the logic circuit 19 is connected by suitable leads L3–L6 with the battery 19, tilt sensor 17 and stimulator circuit 20.

For simplicity, lead L3 from the DC—DC converter is only shown connected to the comparator and filter circuits in FIG. 4, but in reality it powers all elements on the logic circuit board 19.

The transformer 29 functions to increase the low voltage battery to higher voltage and the stimulation circuit 20 produces short energy pulses. It is connected with the electrodes 9, 10 by leads L1 and L2.

The components and functions of the logic circuit 19 are now described.

The tilt sensor 17 produces an analog sensor signal of varying voltage, dependent on its angular position relative to gravity. This sensor signal is transmitted to the filter circuit 21 through lead L7. The signal is filtered by a standard R.C. filter circuit 21. It has values of: R=82 Kohms, C=1.0 $\mu$F. The filter R.C. circuit 21 removes the higher frequency acceleration signals.

The filtered sensor signal is then amplified by operational amplifier 22. The amplifier used is available from Texas Instruments under designation TLC 274. The amplifier 22 increases the output voltage by 10 to 20 times.

The amplified sensor signal is then filtered by a second R.C. filter circuit 23, which has values of R=82 Kohms and C=1.0 $\mu$F. Together the circuits 21 and 23 comprise a second-order low-pass R.C. filter with a cutoff frequency of 2 Hz.

The filtered, amplified (i.e. "conditioned") sensor signal is transmitted from filter R.C. circuit 23 to comparator circuit 24. The signal is an analog one, delivered in volts. The comparator circuit 24 signals activation or deactivation of the stimulator circuit by emitting a digital control signal via lead L6. The comparator circuit used is available from Texas Instruments under the designation TLC 274.

The comparator circuit 24 compares the conditioned sensor signal voltage with an angular ON threshold and operates to activate the stimulator circuit when the threshold is exceeded. A potentiometer 25 enables adjustment of the angular ON threshold. The potentiometer used is available from R. S. Components Ltd., Corby, Northants., U.K., under the designation 186-974.

The comparator circuit 24 also compares the conditioned sensor signal voltage with an angular OFF threshold and operates to deactivate or turn off the stimulator circuit 20 if the voltage drops below this threshold. Potentiometer 30 (also available from R. S. Components) provides a variable amount of hysteresis. In other words, the angular OFF threshold will differ from the ON signal by an amount between 0 and 0.5 volts, depending on the setting of the potentiometer 30.

Thus, the comparator circuit 24 emits a HI control signal (3 volts) when the conditioned sensor signal voltage becomes greater than the angular ON voltage (ON threshold) and a LOW control signal (0 volts) when the voltage becomes less than the angular OFF voltage (OFF threshold).

The digital control signal is delivered via L6 to a timer circuit 26 (the function of which is described below) and thereafter to a lock-out circuit 27. Once the control signal is gated LOW (stimulation to be deactivated), there is a further time, referred to as the lock-out period, during which the lock-out circuit, via lead L5, prevents re-activation of the stimulus. The lock-out circuit used is available from Motorola Semiconductor Products Inc., Austin Tex. under designation CD4538. Lock-out normally occurs at about the time that the heel strikes the ground (see FIG. 5), which gives rise to some oscillation (known as "clonus"). During clonus, even if the conditioned signal were to reach the angular ON threshold, the lock-out circuit 27 functions to continue to gate the comparator output LOW to prevent premature re-triggering of the stimulator circuit 20. The lock-out time can be adjusted between 0.1 and 1 second, using the potentiometer 32 (available from R. S Components).

Thus, the comparator and lock-out circuits 24, 27 monitor the digital control signals and the comparator delivers a HI or a LOW digital signal, as appropriate, to the stimulator circuit 20. More particularly, the comparator circuit 24 delivers a HI signal to the stimulator circuit to turn stimulation ON. The comparator circuit delivers a LOW signal to turn the stimulation OFF. The OFF or LOW signal is processed through the lock-out circuit to introduce the appropriate delay.

In some instances during walking, the patient's leg may not exhibit an angular OFF control signal which occurs early enough in time to properly deactivate the stimulator circuit 20. Therefore, in an alternate embodiment, the stimulator circuit may be deactivated by measuring the time which has elapsed, since the comparator 24 first signalled activation of the stimulation circuit, and comparing it against a maximum elapsed time threshold.

More particularly, the timer circuit 26 is configured to allow adjustment of the maximum allowable elapsed time from 0.2 seconds to 4 seconds using potentiometer 31 (available from R. S. Components). The timer circuit used is available from Motorola under designation CD4538.

If the conditioned signal voltage does not go below the angular OFF threshold before reaching the maximum time threshold set by timer circuit 26, the comparator circuit 24 digital HI signal is gated LOW, signalling deactivation of the stimulator circuit 20, subject of course to the lock-out circuit 27.

Thus, each of the parameters—angular ON and OFF thresholds, maximum time threshold and lock-out period—are adjustable through the potentiometers 25, 30, 31, and 32 respectively.

A socket 33 is provided in the design so that the signals can be brought from the logic circuit to a digital computer for ease of adjusting the potentiometers and sensor data, as described later. Another socket 37 is also provided for connecting a hand or foot switch, should some patients be unable to use a tilt sensor due to the inability to generate sufficient tilt of the lower leg. The circuitry for processing these signals is not novel and is not detailed in FIG. 4. Essentially, inserting a hand or foot switch into the jack disables the filter and amplifier circuits and the alternative devices are connected directly to the comparator circuit 24. A choice of sensors provides flexibility to the preferred design.

The stimulator circuit 20 receives the digital control signal and delivers a series of stimuli (approximately 0.3 ms pulses at 40 ms intervals) through the electrodes 9, 10 for a period when the control signal remains HI. Also shown in FIG. 2 are an amplitude control 34 for adjusting the strength of the stimulus (0–100 mA) and a switch 35 for turning the stimulator and logic circuitry on and off. A suitable stimulator circuit, for this purpose, is available from Institute Josef Stefan under designation Mikrofes Stimulator.

Figure 5:
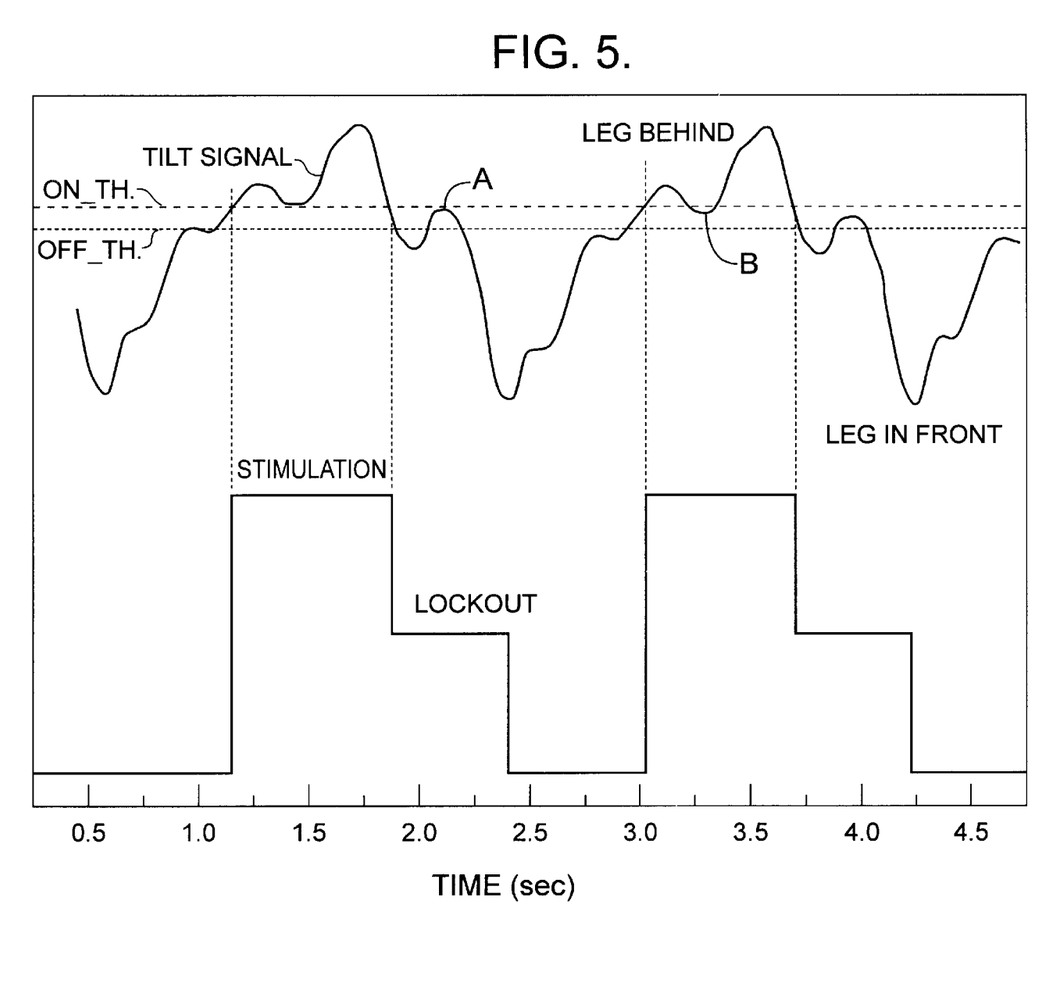
FIG. 5 is a diagram showing the operation of the logic circuitry in conjunction with data recorded from a patient user.

Reliable operation, even for persons whose movement is weak or who have considerable clonus (oscillation), is obtained as shown in FIG. 5. This Figure illustrates two complete step cycles of a person using the device described in the embodiment above. The conditional tilt signal (after amplification and filtering) is illustrated by the solid line in the top part of the Figure. It increases as the body rotates over the leg, while the leg is on the ground during the stance phase of the step cycle. When the leg is behind the body, the angular ON threshold is exceeded (ONTH. in FIG. 5) and stimulation begins. Stimulation continues until 1) the tilt signal falls below the angular OFF threshold (OFFTH. in FIG. 5), as the leg is brought in front of the body during the swing phase of the step cycle, or 2) the maximum time threshold set by the timer circuit 26 is exceeded (not occurring in FIG. 5). The lockout circuit 27 prevents a subsequent re-triggering of the stimulation for a period of time, even if oscillations in the tilt signal reach the angular ON threshold (point A). The presence of hysteresis (the difference between the angular ON and OFF thresholds) prevents the stimulus from turning off prematurely should the stimulus happen to fall below the angular ON threshold, but not below the OFF threshold (point B).

Determination of stimulation requirements for proper limb movement is dependent, in part, upon the nature of the person's disability, the clarity of the signals received and differing physiological conditions such as walking speed and terrain. Accordingly, to avoid subjecting a patient to repeated trial and error testing, it may be necessary to adjust several control circuit parameters which affect initiation and termination of limb stimulation, including angular ON and OFF thresholds and time thresholds such as maximum stimulation time and lockout time.

Set-points for stimulus initiation and termination can be represented by a template which define the state of stimulation as being either ON or OFF, as a function of angle and time. By comparing the state of the stimulator circuit control output against the template, performance can be assessed and optimal adjustment for the control parameter settings can be predicted.

One such template is defined by a trained clinician who, by observing the gait of a patient and using a hand on/off switch, signals when stimulus should optimally be in an ON or OFF state. Alternately, a foot switch or one or more foot sensors can be temporarily employed during testing.

A foot switch produces either and ON or an OFF signal and indicates when the foot lifts from the ground and subsequently strikes the ground. A foot sensor produces a continuous and variable analog signal proportional to a foot's force against the ground. As a result, the position of the foot is somewhat less certain. By specifying a signal threshold, the signal can be analyzed to convert it to a binary ON/OFF or HI/LOW signal. More specifically, the threshold is set so that the signal is HI when the foot leaves the ground (force is lower than the threshold). The signal is set to LOW when the foot is lowered on to the ground and the signal falls below the threshold (force is greater than the threshold).

Once it has been determined that the foot is on or off of the ground, it must be established whether stimulation should be ON or OFF. Optimally, stimulation occurs a short time after the foot's heel leaves the ground and is terminated a short time after the heel strikes the ground. Thus, a template patterned after a foot switch or sensor would incorporate appropriate time delays.

The optimal state of stimulation, defined either by a hand switch or foot switch, is stored by a digital computer for subsequent analysis.

The ON or OFF state of the limb stimulation, as established by a hand switch or foot switch template is compared with that produced by the stimulator circuit for a stored set of tilt sensor test data, from a trial, comprising a plurality of step cycles. As shown in Table 1 below, four conditions are possible; an "error" representing that situation where the active circuit-generated state is inconsistent with the template-predicted state.

TABLE 1

| | TEMPLATE | STIMULATOR output | ERROR |
|---|---|---|---|
| 1) | ON | ON | correct |
| 2) | ON | OFF | incorrect |
| 3) | OFF | ON | incorrect |
| 4) | OFF | OFF | correct |

The results are optimal when the percentage of recorded data in which the incorrect stimulation occurs during the trial (conditions 2 and 3) is minimized.

The stimulus ON and OFF signal is responsive to a multiplicity of parameters, four of which are: ON and OFF thresholds based on tilt angle; maximal permitted time of stimulation (maximum time OFF threshold); and lockout time at heel strike.

It is conceivable that variations in these four and other parameters can be made to improve or optimize the stimulator circuit performance as compared to the template.

One approach to optimize multiple parameters is to apply a gradient-search technique. An error value is calculated as being the percentage of data samples having incorrect stimulation over the total number of samples for the set. The optimization approach is then applied to minimize the error value for a set of step cycles deemed representative of the person's gait.

A gradient-search basically varies the value of one parameter at a time and observes its effect on the error, seeking the greatest decrease (steepest descent) in error. When all parameters have been varied, without further decrease in error, the step size or magnitude of the variation is reduced and the process is repeated. Generally, the gradient-search optimization is performed as follows:

obtain and store a set of data samples for the patient comprising a plurality of uniform step cycles;

establish the initial magnitude of variation to be applied to each parameter, being typically ½ or 50% of the difference between the current value of the parameter and its maximal range or value experienced in the set of data samples;

starting with the parameters that were last used (ie. the settings used during the patient's trials), vary each parameter by the magnitude of its variation, apply it to the data and re-calculate the error (try both increasing and decreasing the value);

If the error is successfully decreased, then that new value for the parameter which produced the greatest reduction in the error is substituted;

repeat the process until the error cannot be reduced further; and reduce the magnitude of the variation applied to each parameter by ½ and repeat the above. Typically, once the magnitude of the variation has been reduced to about 1%, no further significant optimization of the error is apparent.

The optimized parameters are then input at the logic circuit board for use by the patient. These values are then used by logic board 19 as the pre-determined adjustable threshold values. The values are input by manually adjusting physical potentiometers (as shown in FIG. 4), or by automatically adjusting microprocessor-based set-points representing each of the stimulation control parameters.

The stimulation parameters, described above, are used for adjusting angular ON and OFF thresholds, time thresholds and lock-out time. These four parameters are sufficient for most cases, but other parameters could be added including the degree to which the signal is filtered.

Optimization of the stimulation parameters is demonstrated in the following example.

Figure 6:
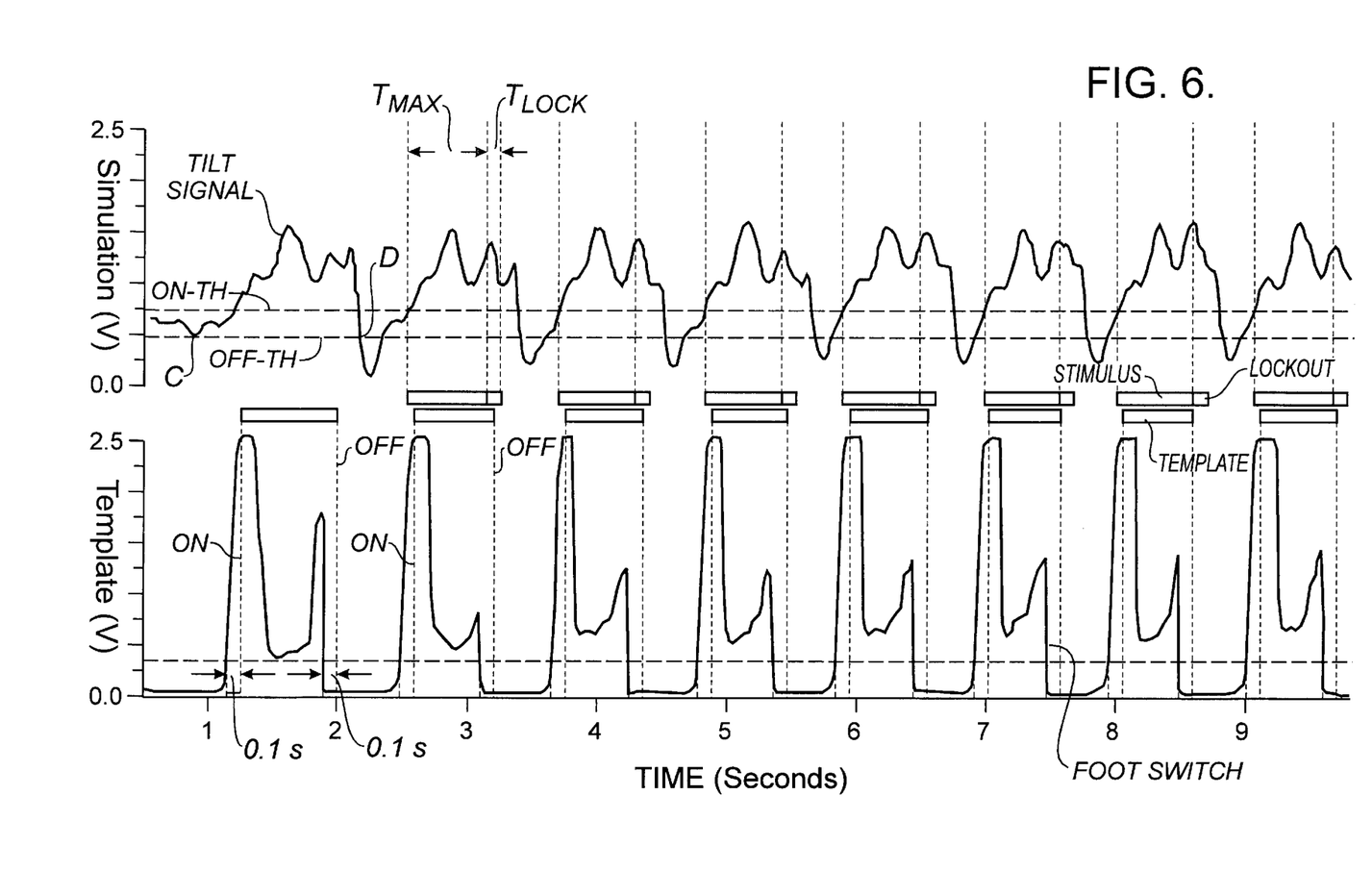
FIGS. 6 and 7 are diagrams showing the operation of the logic circuitry for data recorded from a patient according to original parameters (FIG. 6) and optimized parameters (FIG. 7) as they relate to the Example.
Figure 7:
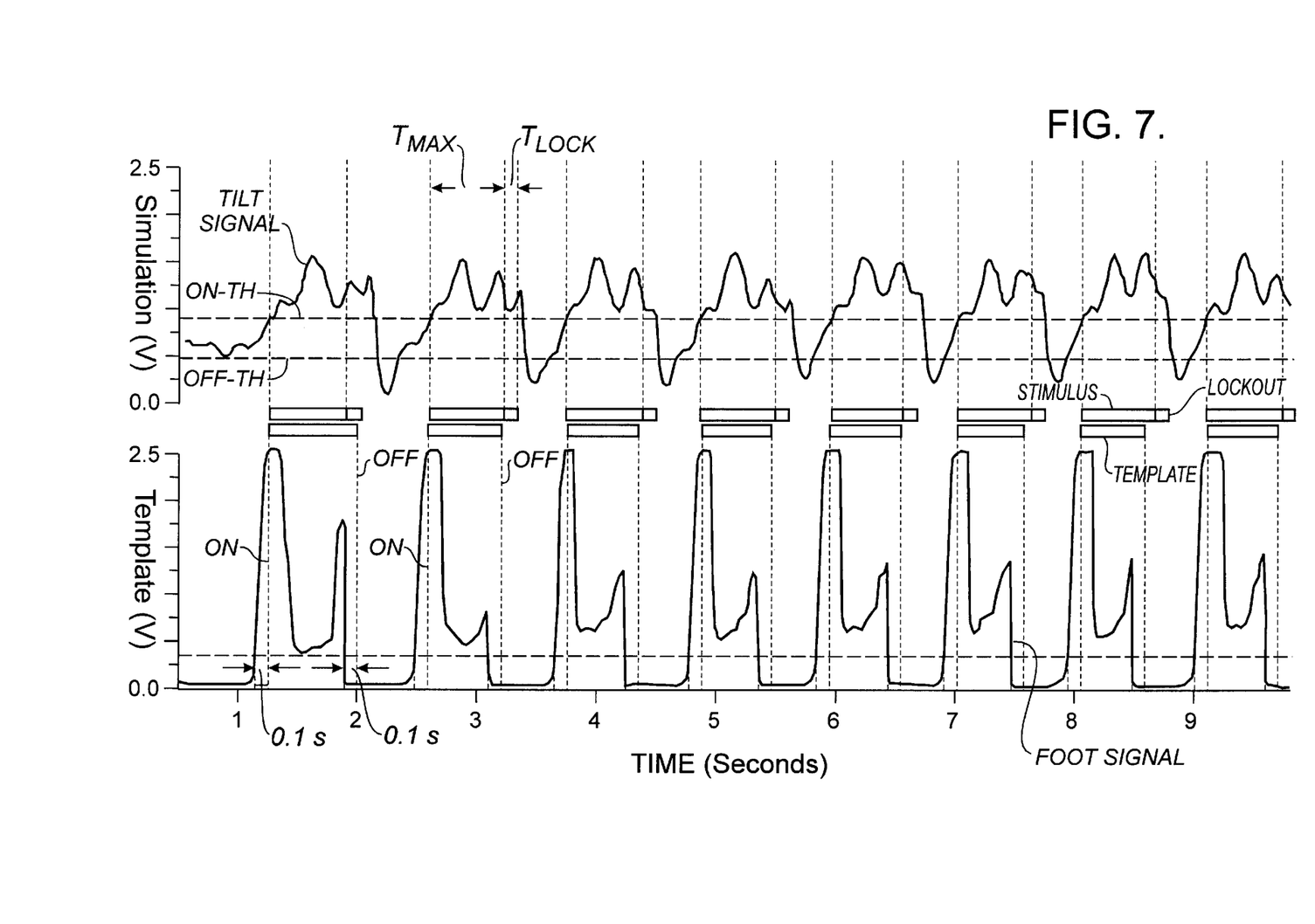

Walking data for one patient is shown in FIGS. 6 and 7. The patient was fitted with a tilt sensor and a foot switch. A 10 second period of tilt signal and foot switch samples was selected, representing eight of the patient's 8 step cycles.

A template was established using the foot sensor data. Foot sensor data below a 0.38 volts threshold (range of 0.0 to 2.5 volts) was interpreted as the foot being on the ground (signal LOW) and data above 0.38 volts was interpreted as the foot being off of the ground (signal HI). Further, a delay of 0.1 seconds was applied for defining the stimulation template from the HI/LOW data signal. More specifically, as shown in FIGS. 6 and 7, the template dictates that optimally, the leg stimulation should be initiated 0.1 seconds after foot off (at signal HI or >0.38 V) and be terminated 0.1 seconds after the foot touches down (at signal LOW or <0.38 V).

Unlike the data presented in FIG. 5, the tilt sensor data of this particular patient did not exhibit a suitably timed angular OFF threshold (OFFTH) and instead, leg stimulation was terminated after the maximum time OFF threshold, set (Tmax) by the timer circuit 26, was exceeded.

As seen in FIG. 6, of the eight step cycles, the actual stimulation was only applied in seven of the cycles; from about 2 seconds on. Practically, this means that the patient's foot was not stimulated for assisting in the flexing of the foot for clearing the ground during the forward swing phase of the leg. This occurred because the previous cycle of the leg did not cause the tilt sensor to reach the angular OFF threshold (point C) specified by the potentiometer setting for clearly indicating the termination of the patient's step cycle. It was only at about 2 seconds (point D) that the leg angle did finally drop below the OFF threshold and the end of a step cycle was clearly delineated.

The original and optimized parameters are presented in Table 2 below:

TABLE 2

|  | ORIGINAL | OPTIMIZED |
| --- | --- | --- |
| ON_TH | 5° | 10° |
| OFF_TH | −5° | −8° |
| T max | 0.53 s | 0.62 s |
| T lock | 0.14 s | 0.14 s |
| Total Error | 14% | 5% |

As shown in FIG. 6, when the patient was tested with the original parameter settings, the stimulator circuit demonstrated a 14% error when compared to the template. The missed first step contributed greatly to the larger error. After optimization (FIG. 7), the error was reduced to 5% by varying three of the four parameters noticeably, namely, the tilt angle sensor ON and OFF thresholds (ONTH, OFF TH) and the maximum stimulation time (Tmax). In particular, it was the raising of the OFFTH from −5° to −8° which captured the first step cycle and would result in improved stimulation performance in future walking trials.

Clearly, while additional trials may be still performed to fine tune the parameters or define a set of parameters for differing physiological conditions, optimization can be achieved without unduly subjecting the patient to the large number of iterations that the optimization process can perform.

The embodiments of the invention in which an exclusive property or privilege is claimed are defined as follows:

1. A functional electrical stimulator for use on a body limb, comprising:

a band, mountable on the limb, for carrying stimulator components;

cathode and anode electrodes carried by the band in a fixed condition;

means, carried by the band, for reproducibly positioning the band so that the electrodes are located at specified stimulation locations;

sensor means, carried by the band in a fixed condition, for measuring the angular position of the limb during movement and emitting sensor signals indicative thereof;

control circuit means, carried by the band and connected with the sensor means and electrodes, for receiving the sensor signals, processing the sensor signals to establish values indicative of the changing angularity of the limb as a function of time and to compare the established values with predetermined adjustable angular ON and OFF and time threshold values for initiating and terminating the emission of pulses through the electrodes when the established values reach the angular ON and OFF and time threshold values, to stimulate the limb; and battery means carried by the band and connected with the sensor means and control circuit means, for supplying electrical power to them.

2. A process for determining new angular ON and OFF and time threshold values for the control circuit means of the functional electrical stimulator defined by claim 1, comprising:

storing the sensor signals for the angular position of a user's limb during movement as a function of time;

storing template values indicative of the states of stimulation which are required for proper movement of the user's limb, as a function of time;

processing the stored angular sensor signals using the control circuit means to establish values indicative of the changing angularity of the limb as a function of time and comparing the established values with predetermined angular and time threshold values so as to determine values indicative of the state of stimulation of the limb as the established values reach the angular ON and OFF and time threshold values;

comparing the state of stimulation as determined by the established values and by the template values as a function of time and storing any disparity there between as an error value;

minimizing the error value by adjusting the angular ON and OFF and time thresholds; and adjusting the angular ON and OFF and time threshold values which are compared by the control circuit means for improved performance at the user's limb.

3. The process for determining new angular ON and OFF and time thresholds as recited in claim 2 wherein the stimulator is used by a patient and the template values are input by a clinician observing the patient using the stimulator.

4. The process for determining new angular ON and OFF and time thresholds as recited in claim 2 wherein the stimulator is used by a patient and the template values are provided by foot sensor means worn by the patient and connected with the control circuit means.

5. A process for determining new ON and OFF threshold values and elapsed time values for the control circuit means of the functional electrical stimulator defined by claim 1, comprising:

providing temporary means for inputting to the control circuit means template values indicative of the state of stimulation of the limb, during the limb movement, required for proper limb movement;

simultaneously sensing the angular position of the limb during the limb movement and emitting angular sensor signals indicative thereof;

storing the template values;

storing the angular sensor signals;

processing the stored angular sensor signals using the control circuit means to establish values indicative of the changing angularity of the limb as a function of time and comparing the established values with predetermined ON and OFF threshold values and elapsed time values and establishing values indicative of the state of stimulation of the limb as the established values reach the angular ON and OFF and time threshold values;

comparing the state of stimulation as determined by the established values and the required state of stimulation as determined by the template values as a function of time and storing any disparity there between as a first error value;

systematically selecting new angular ON and OFF and time threshold values, re-processing the stored sensor signals and re-comparing both the newly determined stage of stimulation and the template stage of stimulation as a function of time and storing any disparity there between as a second error value;

comparing the first and second error values and selecting the angular ON and OFF and time threshold values which minimize the error signal;

repeatably and systematically selecting new ON and OFF threshold values and elapsed time values and comparing the first and second error values until they are minimized; and adjusting the ON and OFF threshold values and elapsed time values used with the control circuit means accordingly for subsequent use on the body limb.

6. A functional electrical stimulator for use on a body limb, comprising:

a band, mountable on the limb, for carrying stimulator components;

cathode and anode electrodes carried by the band in a fixed condition;

means, carried by the band, for reproducibly positioning the band so that the electrodes are located at specified stimulation locations;

sensor means, carried by the band in a fixed condition, for measuring the angular position of the limb during movement and emitting sensor signals indicative thereof;

control circuit means, carried by the band and connected with the sensor means and electrodes, for receiving the sensor signals and processing the sensor signals to establish values indicative of the changing angularity of the limb, comparing the established values with predetermined adjustable ON and OFF threshold values and initiating the emission of pulses through the electrodes when the established values reach the ON threshold values to stimulate the limb, terminating the emission of pulses through the electrodes when the established values reach the OFF threshold values, measuring stimulation-ON elapsed time which is initiated when the limb is stimulated, comparing the stimulation-ON elapsed time with a predetermined maximum time and terminating the emission of pulses through the electrodes after said pre-determined maximum time, even if the sensor signal values have not reached the OFF threshold value; and battery means, carried by the band and connected with the sensor means and control circuit means, for supplying electrical power to them.

7. A functional electrical stimulator as recited in claim 6 wherein the control circuit means further is operative:

to measure stimulation-OFF elapsed time, initiated when the limb ceases to be stimulated, and compare the stimulation-OFF elapsed time with a predetermined lock-out period and prevents initiation of the emission of pulses through the electrodes until the elapsed time exceeds the pre-determined lock-out period, thereby preventing premature re-initiation of limb stimulation.

\* \* \* \* \*